United States Patent
Zhang et al.

(10) Patent No.: US 12,103,480 B2
(45) Date of Patent: Oct. 1, 2024

(54) OMNI-WHEEL CABLE PUSHER

(71) Applicant: GLOBUS MEDICAL, INC., Audubon, PA (US)

(72) Inventors: Kevin Zhang, Medford, MA (US); Steven Tracy, Litchfield, NH (US); David Toombs, Hollis, NH (US); Gary Pinard, Manchester, NH (US); Norbert Johnson, North Andover, MA (US)

(73) Assignee: Globus Medical Inc., Audubon, PA (US)

( * ) Notice: Subject to any disclaimer, the term of this patent is extended or adjusted under 35 U.S.C. 154(b) by 278 days.

(21) Appl. No.: 17/655,370

(22) Filed: Mar. 18, 2022

(65) Prior Publication Data

US 2023/0294627 A1    Sep. 21, 2023

(51) Int. Cl.
| | |
|---|---|
| *B60R 19/54* | (2006.01) |
| *A61B 6/00* | (2006.01) |
| *B60S 9/14* | (2006.01) |
| *B62B 5/00* | (2006.01) |
| *B60R 19/00* | (2006.01) |

(52) U.S. Cl.
CPC ............ *B60R 19/54* (2013.01); *A61B 6/4405* (2013.01); *B60S 9/14* (2013.01); *B62B 5/0086* (2013.01); *B60B 2200/26* (2013.01); *B60R 2019/002* (2013.01)

(58) Field of Classification Search
CPC ......... B60R 19/54; B60R 19/04; B60R 19/16; B60R 2019/002; A61B 6/4405; B60S 9/14; B62B 5/0086; B62B 5/0083; B60B 220/26
See application file for complete search history.

(56) References Cited

U.S. PATENT DOCUMENTS

| | | | |
|---|---|---|---|
| 2,450,062 A | * | 9/1948 | Voss ........................ B60B 33/00 |
| | | | 280/160 |
| 4,150,293 A | | 4/1979 | Franke |
| 5,246,010 A | | 9/1993 | Gazzara et al. |
| 5,354,314 A | | 10/1994 | Hardy et al. |
| 5,397,323 A | | 3/1995 | Taylor et al. |
| 5,598,453 A | | 1/1997 | Baba et al. |
| 5,702,117 A | * | 12/1997 | Geelhoed ............ B60B 33/0028 |
| | | | 280/160 |
| 5,772,594 A | | 6/1998 | Barrick |
| 5,791,908 A | | 8/1998 | Gillio |
| 5,820,559 A | | 10/1998 | Ng et al. |
| 5,825,982 A | | 10/1998 | Wright et al. |
| 5,887,121 A | | 3/1999 | Funda et al. |

(Continued)

OTHER PUBLICATIONS

US 8,231,638 B2, 07/2012, Swarup et al. (withdrawn)

*Primary Examiner* — John D Walters (57) ABSTRACT

Cable protector devices, assemblies, and systems. The cable protection system may include a moveable system with wheels for moving the moveable system across a floor and a cable pusher attached to each of the wheels. Each cable pusher may include a frame with a pair of deflector legs configured to be positioned in front of and behind each wheel in close proximity to the floor. The cable pusher may be magnetically secured to the wheel, and the deflector legs may magnetically connect to the frame. As the wheels spin or rotate, the frame and deflector legs remain stationary, thereby pushing obstacles out of the way.

20 Claims, 9 Drawing Sheets

(56) References Cited

U.S. PATENT DOCUMENTS

| | | |
|---|---|---|
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |

(56) References Cited

U.S. PATENT DOCUMENTS

| | | |
|---|---|---|
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Arkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Voll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |

(56) References Cited

U.S. PATENT DOCUMENTS

| | | |
|---|---|---|
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,701,269 B1 * | 7/2017 | Dubas ................ B60B 33/0052 |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 11,820,170 B2 * | 11/2023 | Spoelstra ............ B60B 33/0028 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |

(56) References Cited

U.S. PATENT DOCUMENTS

| | | |
|---|---|---|
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Arkin et al. |
| 2011/0224689 A1 | 9/2011 | Arkin et al. |
| 2011/0224825 A1 | 9/2011 | Arkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |

(56) References Cited

U.S. PATENT DOCUMENTS

| | | |
|---|---|---|
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

\* cited by examiner

OMNI-WHEEL CABLE PUSHER

FIELD OF THE INVENTION

The present application relates generally to cable protection systems, and more particularly, to cable pushers configured to protect cables lying on the floor from damage by wheels of a moveable system.

BACKGROUND OF THE INVENTION

The healthcare industry utilizes a number of mobile systems for patient care. In particular, mobile three-dimensional imaging systems, robotic systems, and/or navigation systems may be used in operating rooms, procedure rooms, intensive care units, emergency departments, ambulatory surgery centers, physician offices, or the like. These moveable systems may be very useful during surgery or other procedures.

The imaging, robotic, and/or navigation systems may be moveable via a set of wheels. In some cases, omni-directional wheels may be used to allow for multiple-axis movement of the system. Omni-directional wheels provide for all of the desired degrees of freedom similar to conventional casters but without swiveling. However, the moveable nature of the equipment can pose the problem of potentially damaging nearby cables on the floor. While moving the equipment, the wheels may inadvertently run over cables or leads from various angles including laterally, and the wheels may cause damage to the cables or leads. Accordingly, there is a need to protect various cables and leads lying on the floor from this type of damage.

SUMMARY OF THE INVENTION

To meet this and other needs, cable protection devices, assemblies and systems, moveable systems with cable protectors on the wheels, and methods of installing and using the same are provided. In particular, the cable protection system may utilize features on three of the four sides of each wheel configured to contact and push nearby cables while not allowing them to wander under the wheel. The cable protector device is adaptable to omni-type wheels that provide for multiple-axis movement of the system. The cable protection system protects the wheels from various cables and leads lying flat or slightly raised from the floor that could migrate under the equipment. The cable protection system may push the cables, leads, or wires out of the way, thereby preventing any damage.

According to one embodiment, a cable protection system includes a moveable system with a plurality of wheels for moving the moveable system across a floor, and a cable pusher attached to each of the plurality of wheels. Each cable pusher may include a frame with a pair of deflector legs configured to be positioned in front of and behind each wheel in close proximity to the floor. The cable pusher may be magnetically secured to the wheel. The deflector legs may magnetically connect to the frame. As the wheels spin or rotate, the frame and deflector legs remain stationary, thereby pushing obstacles (such as cables, wires, or leads) out of the way.

The cable protection system may include one or more of the following features. Each deflector leg may include an elongate leg and a shoulder configured to mate with the frame. The shoulder may transition to the leg with a bent portion that positions the leg transverse to the shoulder and the frame when connected thereto. The shoulder may be bifurcated into two branches by a window, and magnets may be positioned in the two branches of the shoulder. The pair of deflector legs may be aligned in parallel to one another. The frame may include an upper hub configured to engage with a wheel hub of the wheel, a pair of angled arms extending distally, and a base connecting the angled arms. The upper hub of the frame may house a spinning magnet constrained inside a magnet retainer such that the spinning magnet attracts to a magnet on the wheel. The cable pusher may be attached to the wheel with a mount including a revolving central shaft and a pair of blades positioned on opposite sides of the central shaft. The wheels may be omni-directional wheels configured to allow for multiple-axis movement of the moveable system. The moveable system may be medical equipment, such as an imaging system, robotic system, and/or navigation system.

According to another embodiment, a cable pusher assembly includes a frame, first and second deflector legs, and a target mount. The frame includes an upper hub, a pair of angled arms, and a base connecting the angled arms. The base includes first and second connection areas each including north and south magnets. The first and second deflector legs each include north and south magnets configured to magnetically attract to the opposite north and south magnets of the first and second connection areas, respectively, thereby securing the first and second deflector legs to the first and second connection areas of the frame. The target mount includes a revolving central shaft and a pair of blades positioned on opposite sides of the central shaft. The upper hub of the frame houses a spinning magnet constrained inside a magnet retainer.

The cable pusher assembly may include one or more of the following features. The central shaft may include an outward projection on a front face of the mount receivable in a seat defining a cavity for the projection. The target mount including the central shaft, the seat, the spinning magnet, and the magnet retainer may be coaxially aligned along a central axis. The base and the deflector legs may include one or more indicators identifying the north and south magnets such that the magnets attract when the deflector legs are correctly positioned against the frame (and repel if not aligned properly). The magnets may be disc magnets or other suitable polar magnets.

According to yet another embodiment, a cable protection system includes a moveable system, a cable pusher, and a lifting jack. The moveable system includes a plurality of wheels for moving the moveable system across a floor. The cable pusher is attachable to one or more of the plurality of wheels. The cable pusher includes a frame with a pair of deflector legs and a mount including a revolving central shaft and a pair of blades positioned on opposite sides of the central shaft. The lifting jack is attachable to one or more of the plurality of wheels. The lifting jack includes a jack mount and a dolly. The lifting jack is configured to lift the wheel off the floor and allow for movement of the moveable system using the dolly.

The cable protection system may include one or more of the following features. The central shaft of the mount may include an outward projection defining a threaded portion configured to theadedly interface with the jack mount. The mount may be securable to the wheel with nuts positioned through openings in the blades of the mount. The lifting jack may include a jacking bolt to raise and lower the wheel. The dolly may include a plate with a plurality of caster wheels.

The lifting jack and dolly may allow for the moveable system to be manually maneuvered upon power loss.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to cable protection devices, assemblies, and systems. Specifically, embodiments are directed to cable protectors or pushers that prevent damage to cables, wires, or leads lying on the floor. The cable protectors may be provided on each wheel of moveable equipment to prevent the wheels from rolling over or catching the cables. The cable protectors may be especially suitable for moveable medical equipment, such as portable medical imaging systems, robotic systems, navigation systems, and the like, although it will be appreciated that the cable protectors may also be used on the wheels of moveable equipment in other applications and industries.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments and modifications thereof are contemplated as falling within the scope of this disclosure and equivalents thereto.

Figure 1:
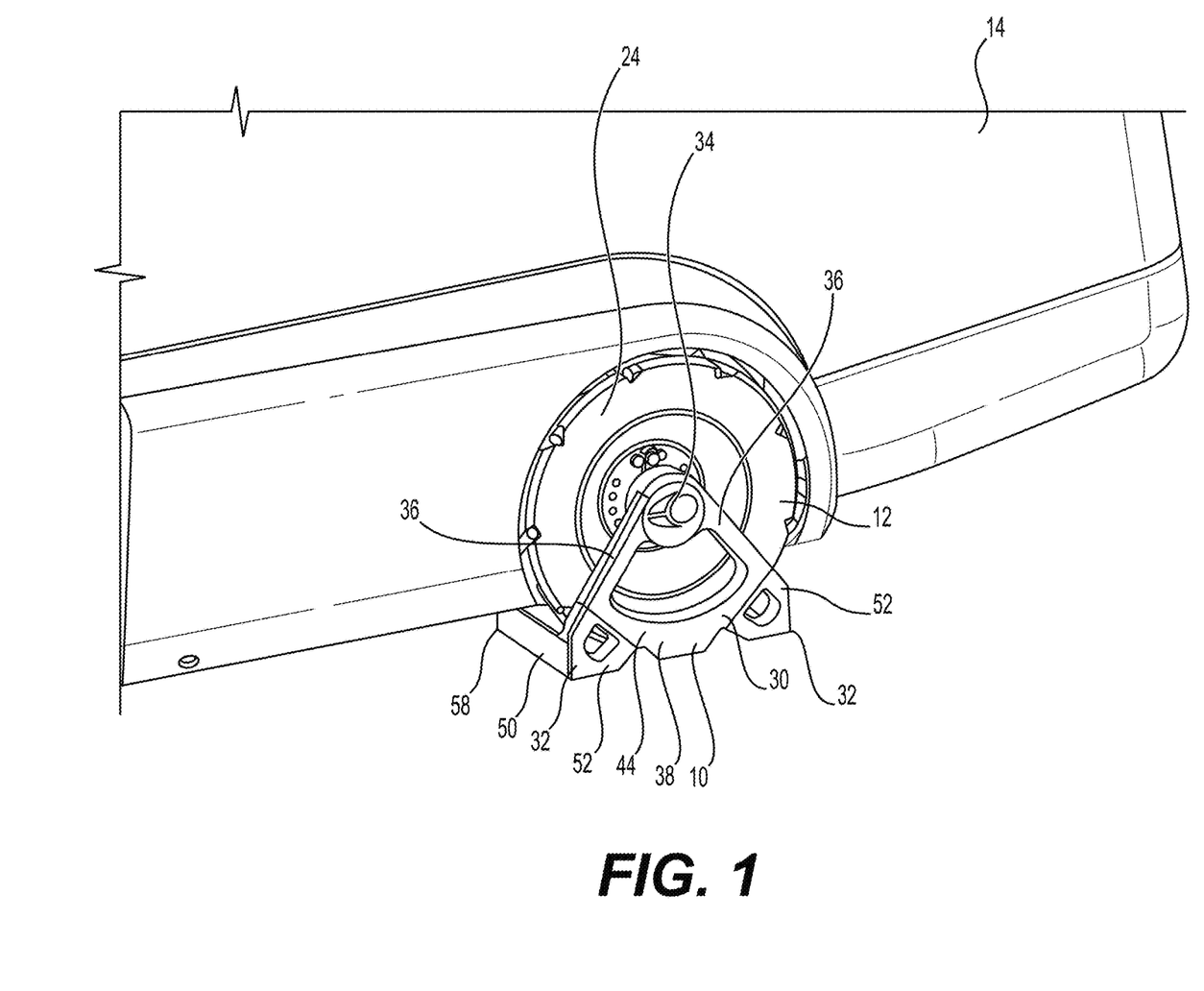
FIG. 1 shows a perspective view of a cable protector coupled to an omni-directional wheel of a moveable system according to one embodiment.

Referring now to FIG. 1, a cable protection system 10 is shown according to one embodiment. The cable protection system 10 is configured to be attached to one or more wheels 12 of moveable medical equipment 14. In one embodiment, the cable protection system 10 may be provided on each of the wheels 12 of the equipment 14. The cable protection system 10 is configured to protect any cable on or near the floor when the medical equipment 14 is moved about the room (e.g., the operating room). The cables may include any cables, wires, or leads in the room, for example, having a protective casing and used for transmitting electricity or telecommunication signals. The cable protection system 10 prevents the tangling or pinching of cables routed along the floor. During motion of the wheels 12, the cable protection system 10 comes into contact with objects first to avoid interference with the wheels 12 by pushing the obstacles out of the way. The cable protection system 10 may be configured to push or guide any cables out of the path of the wheels 12, thereby preventing the wheels 12 from rolling over the cable or the cable getting caught up into the wheels 12.

Figure 2A:
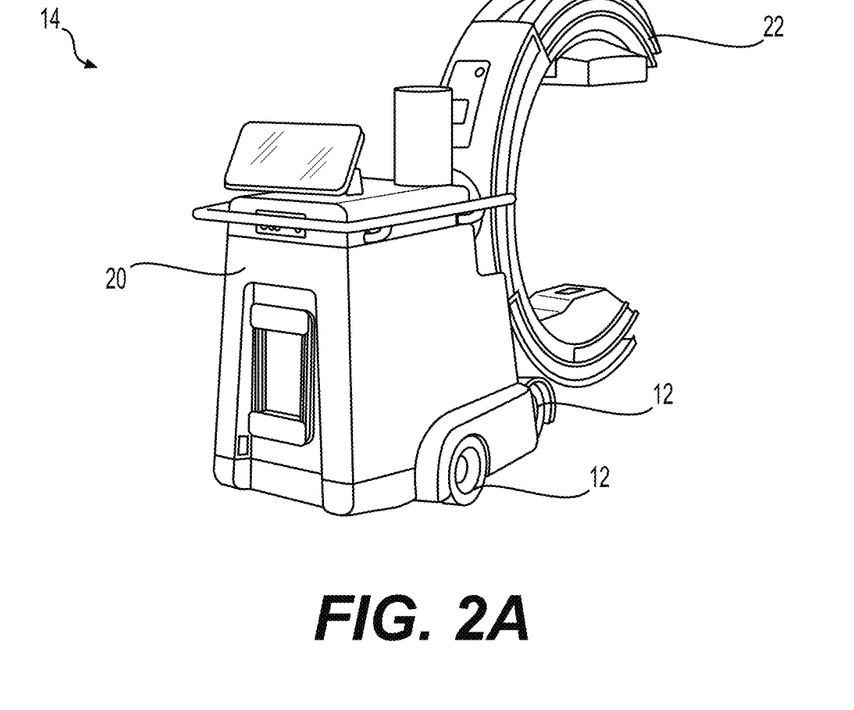
FIGS. 2A-2B show a moveable station and gantry for three-dimensional imaging according to one embodiment.
Figure 2B:
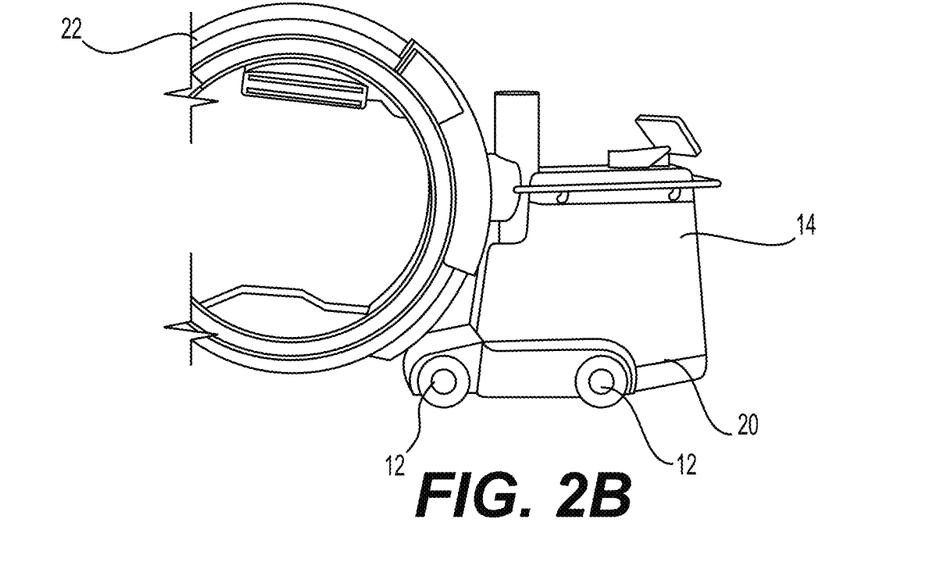

With emphasis on FIGS. 2A-2B, the medical equipment 14 may include a medical imaging system, such as a computerized tomographic (CT) x-ray scanner, including a moveable station 20 and a gantry 22. The movable station 20 may include two front wheels 12 and two rear wheels 12, which together provide movement of the movable station 20 in any direction in an X-Y plane. The gantry 22 may include a first C-arm and a second C-arm slidably coupled to the first C-arm, which are configured to provide imaging modalities including but not limited to, fluoroscopy, 2D radiography, cone-beam CT, and magnetic resonance imaging (MRI). Further details of the medical imaging system 14 is provided in U.S. Pat. No. 10,842,453, which is incorporated by reference herein in its entirety for all purposes. Although a medical imaging system is exemplified, it will be appreciated that other movable medical equipment may be provided with the cable protection systems 10 described herein.

The wheels 12 may include omni-directional wheels, which allow for the movable station 20 to be positioned in all three degrees of freedom about the horizontal plane (X, Y, Wag). The omni-directional wheels 12 allow for positioning in tight spaces, narrow corridors, or for precisely traversing up and down the length of an operating room table or patient bed. The omni-directional wheels 12 may have a central hub 24 with a plurality of smaller wheels or rollers 26 on or around its circumference. The smaller wheels 26 may be mounted at an angle to the central axis of the hub 24, thereby allowing for movement in any direction. Each wheel 12 may be powered individually to guide the portable medical imaging cart 20 in the desired direction. Further details of suitable types of omni-directional wheels 12 are provided in U.S. Pat. No. 10,842,453, which is incorporated by reference herein in its entirety for all purposes.

The medical equipment 14 is configured to move about the room via wheels 12. The equipment 14 may be moved by a person and/or with motor control. There may be cables, wire, and/or leads on or near the floor of the room, for example, from the medical equipment itself and other medical equipment used in the space. As the medical equipment 14 is moved about the space, it is desired that the wheels 12 do not run over, pinch, or otherwise damage the cables. Cable protectors or pushers 10 may be provided on each wheel 12 to prevent contact between the wheels 12 and the cables. For example, the cable pushers 10 may push or move the cables out of the way as the medical equipment 14 moves about the room.

Figure 3:
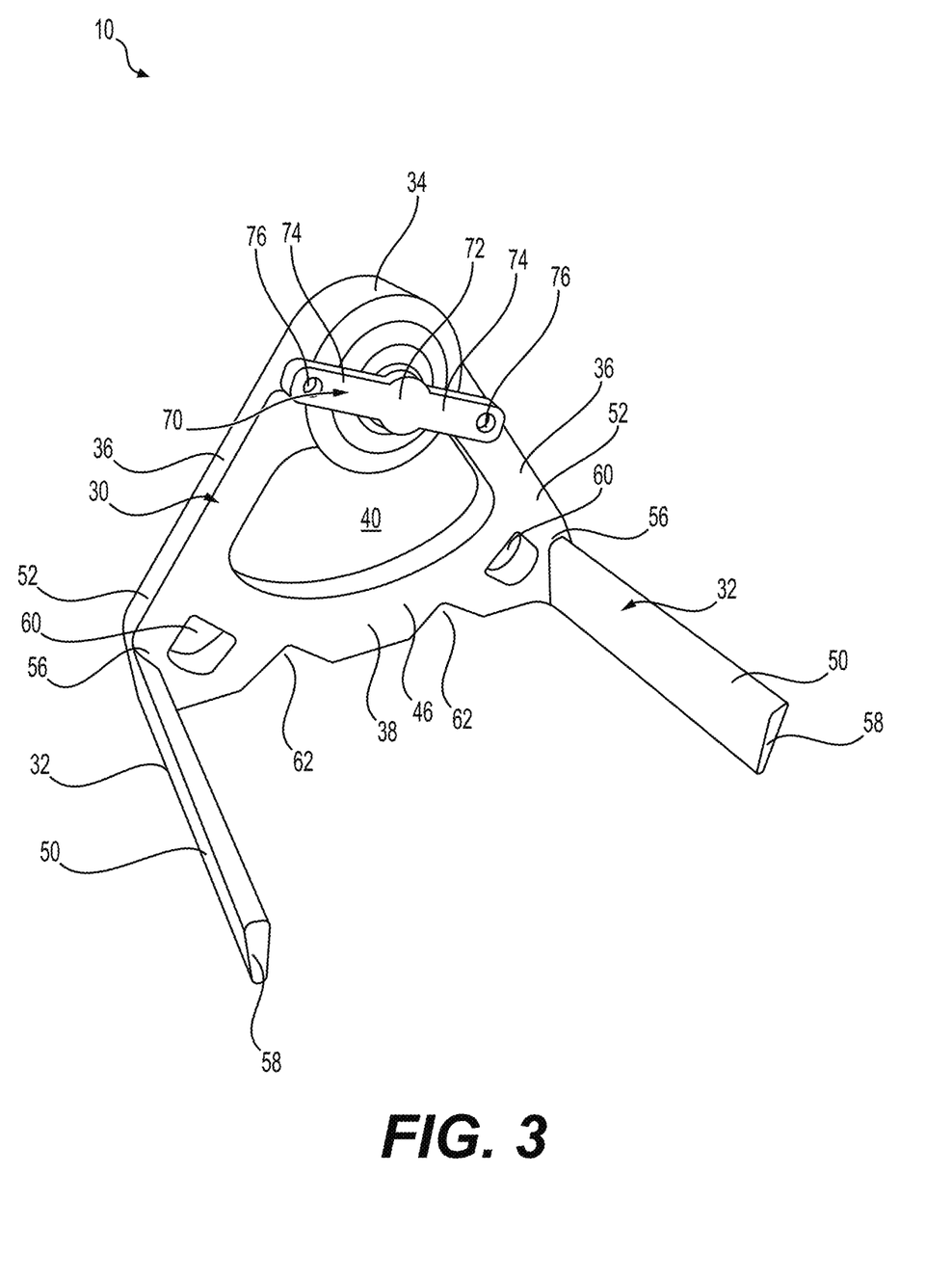
FIG. 3 is a perspective view of the cable protector according to one embodiment.

With emphasis on FIG. 3, the cable protector or pusher assembly 10 is shown in more detail. The cable protector assembly 10 includes a frame 30 with one or more deflector legs 32. The frame 30 includes an upper hub 34 configured to engage with the wheel hub 24 of the wheel 12. The outer body of the upper hub 34 may be generally rounded or curved. For example, the upper hub 34 may have a generally cylindrical body. The frame 30 may include a pair of angled arms 36 extending downwardly or distally. Each arm 36 may be angled about 20-45°, about 30-45°, or about 30° from a central longitudinal axis of the frame 30. The angled arms 36 may form a generally triangular or A-frame type configuration for the frame 30.

The distal end of each arm 36 may be connected to one another with a base 38. The frame 30 may define a cutout 40 between the hub 34, arms 36, and base 38. The cutout 40 may be generally straight along arms 36 and curved along hub 34 and base 38. The curved portion of the cutout 40 along the base 38 may be concave and the curved portion of the cutout 40 along the hub 34 may be convex. The base 38 may be segmented with a first connection portion 42 near the distal end of the first arm 36 and a second connection portion 42 near the distal end of the second arm 36. The connection portions 42 are configured to secure first and second deflector legs 32, respectively. A central portion of the base 38 between the two connection portions 42 may be configured to contact or be in close proximity to the floor.

The frame 30 has an outward-facing face 44 and an opposite inward facing face 46. The inward face 46 is configured to face toward the wheel hub 24 when the cable protector 10 is attached to the wheel 12. The outward face 44 may have a generally planar surface. The components of the frame 30 may be formed from a solid material or may be separate components that are joined together, for example, with pins, adhesive, or the like. The cable protector 10 may be formed from metals, such as steel, aluminum, or iron; plastics, such as polyurethane or polyvinylchloride; rubber; or combinations thereof.

Each deflector leg 32 includes an elongate blade or leg 50 and a shoulder 52. The shoulder 52 includes connection portion 54 configured to mate with the corresponding connections portions 42 on the frame 30. The shoulder 52 transitions to the leg 50 with an angled or bent portion 56. The bent portion 56 may be offset to one side of the shoulder 52. The bent portion 56 positions the leg 50 transverse to the shoulder 52 and body of the frame 30 when connected thereto. For example, the bent portion 56 may be angled about 80-100°, or about 90° such that the leg 50 extends generally perpendicular to the shoulder 52 and body of the frame 30 when connected thereto. Each blade or leg 50 terminates at a free end 58. When the cable protector 10 is attached to the wheel 12, the leg 50 is configured to extend back and under the wheel 12. Thus, the length of the leg 50 may be equal to or greater than the width of the wheel 12, thereby providing adequate protection to the wheel 12. With two legs 32 attached to the frame 30 (i.e., left and right deflector legs 32), the legs 50 are positioned in front of and behind the wheel 12, respectively. The pair of legs 50 may be aligned generally in parallel to one another. Each leg 50 also has a height configured to block any cables or leads lying on or near the floor. The legs 50 may be slightly angled away from one another such that the top of each leg 50 is further away from one another and the bottom of each leg 50 closer together. In this manner, the legs 50 protect the wheel 12 during travel in any direction.

To assist in assembly and/or with visibility, each shoulder 52 may define a cutout or window 60. The window 60 may bifurcate the shoulder 52 into two branches configured to receive the magnets 90, 92. The window 60 may form an arch shape with rounded corners. The connection portion 54 may form a flat face configured to mate against a corresponding flat face of the connection portion 42 on the frame 30. When the legs 32 are coupled to the frame 30, notches 62 may be defined between the shoulder 52 and the base 38 of the frame 30. The notches 62 may be generally triangular in shape. The notches 62 may be formed on the underside of the cable protector assembly 10, thereby providing clearance from the floor.

The cable pusher assembly 10 may be attached to the wheel 12 with a mount 70. The mount 70 may form a spinning target mount including a revolving central shaft 72 with one or more blades 74. The central shaft 72 may include a projection 73 on the front face of the mount 70. The projection 73 may define a circular or cylindrical interface. In one embodiment, a pair of blades 74 are aligned with one another on opposite sides of the shaft. 72. Although two blades 74 are exemplified, it will be appreciated that the mount 70 may include a suitable number of blades 74 or other geometry to secure the cable pusher assembly 10 to the wheel assembly 12. When attached to the wheel 12, the mount 70 is configured to revolve such that the mount 70 keeps pace with the revolution of the wheel 12 while holding the frame 30 and legs 32 steady.

The mount 70 may be secured to the wheel 12 with one or more fastening mechanisms. In one embodiment, the mount 70 is magnetically attracted to the wheel hub 24. In this manner, the cable pusher assembly 10 can be easily attached and removed by hand, without any tools. The mount 70 may also be attached with one or more fasteners, such as screws, bolts, or nuts 104. Openings 76 may be provided near the free end of each blade 74. The openings 76 may be configured to receive the respective fasteners, thereby allowing the mount 70 to be optionally bolted to the wheel hub 24.

Figure 4:
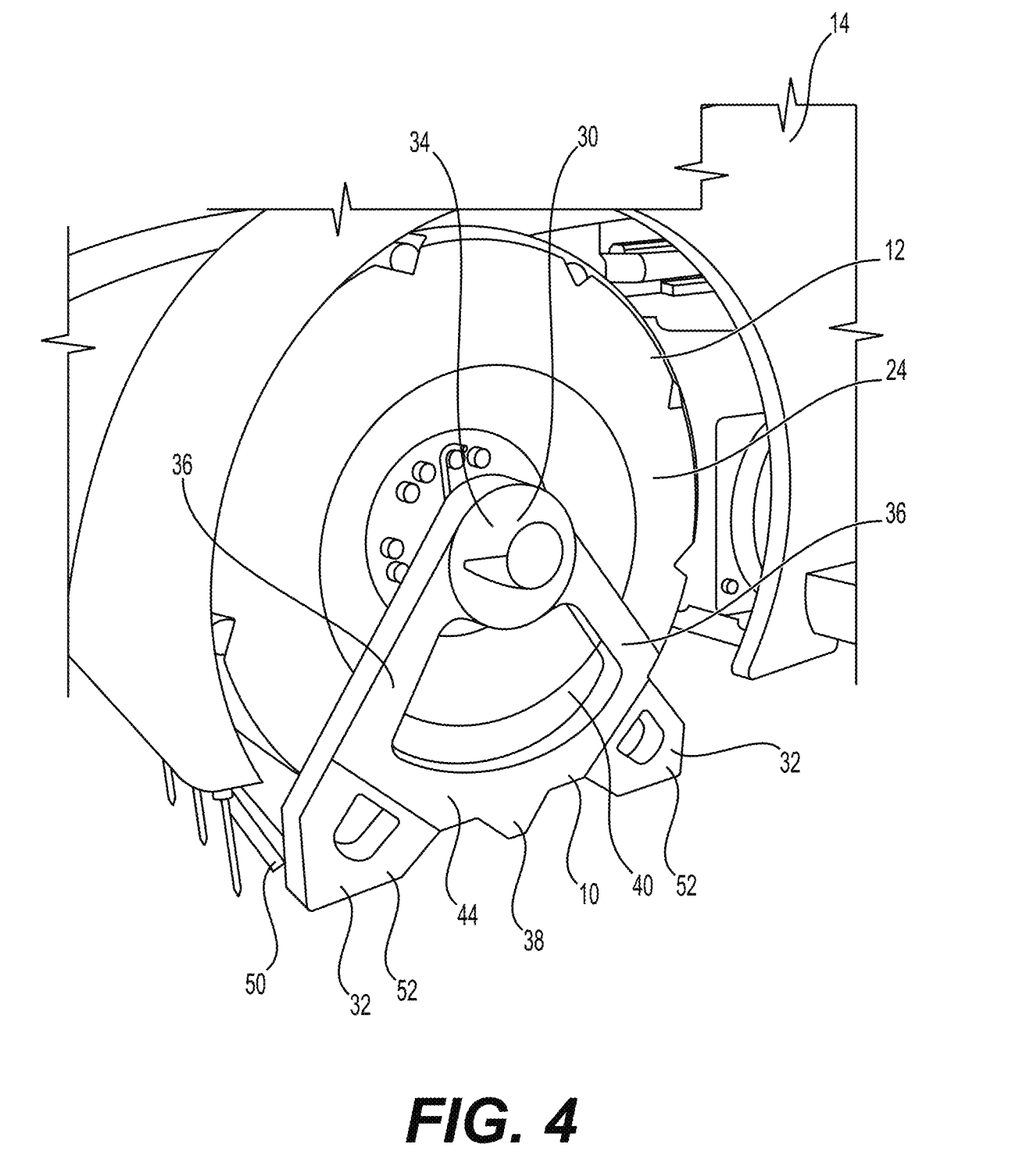
FIG. 4 shows the cable protector mounted to the wheel hub of the omni-wheel of the moveable system according to one embodiment.
Figure 5:
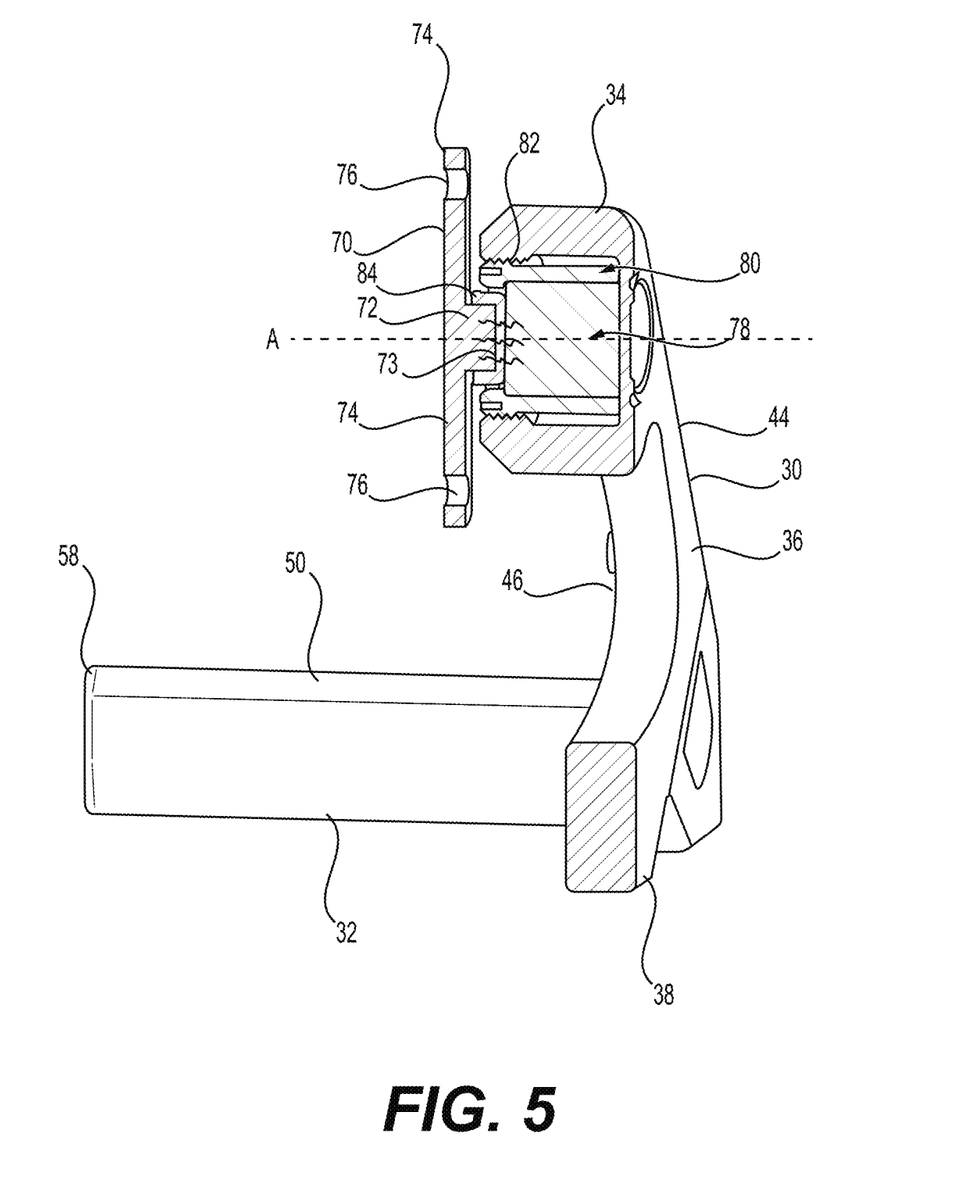
FIG. 5 shows a partial cross-sectional view of the cable protector with the magnetically attracted mount and constrained spinning magnet according to one embodiment.

As best seen in FIG. 4, when attached to the wheel assembly 12, the mount 70 allows for the deflector legs 32 to hang slightly off the floor vertically and stationary while the wheel 12 spins. This may be accomplished using the magnetically attracted mount 70 with an internally constrained spinning magnet 78. As best seen in FIG. 5, the spinning magnet 78 may be held inside a magnet retainer 80. The internally constrained spinning magnet 78 may be positioned inside the hub 34 of the frame 30. The magnet retainer 80 may have a threaded interface 82 with the frame hub 34. The internally constrained spinning magnet 78 acts as a shaft that attracts to a ferrous target on the wheel's center hub 24.

The mount 70 may be separated from the frame 30 and magnetically attracted to the frame 30 via the constrained magnet 78. The outward projection 73 of the mount 70 is receivable in a seat 84 which defines a cavity for receiving the projection 73. The seat 84 may be sandwiched between the projection 73 and the constrained magnet 78. The mount 70 including shaft 72, seat 84, spinning magnet 78, and magnet retainer 80 may be coaxially aligned along central axis A. The spinning magnetic target mount 70 magnetically attaches to the wheel hub 24. When the assembly 10 is attached to the wheel 12, the central axis A is aligned to and corresponds with the central rotational axis of the wheel hub 24. As the wheel 12 spins or rotates, the frame 30 and deflector legs 32 remain stationary, thereby pushing any obstacles out of the way.

The cable pusher assembly 10 is configured to easily detach as a whole from each wheel 12 so that the cable pusher assemblies 10 can be quickly removed prior to traversing over a fixed or rigid obstacle, such as a threshold. In the event that the cable pusher assemblies 10 are forgotten to be removed and inadvertently run into a threshold, each deflector leg 32 may utilize a magnetic break-away interface in order to prevent serious damage to the equipment 14 as well as the cable pusher assembly themselves. Upon impact, the deflector legs 32 may detach while the main frame 30 rotates on the wheel 12. A quick reassembling and mounting gets the deflector legs 32 back to being operational.

Figure 6A:
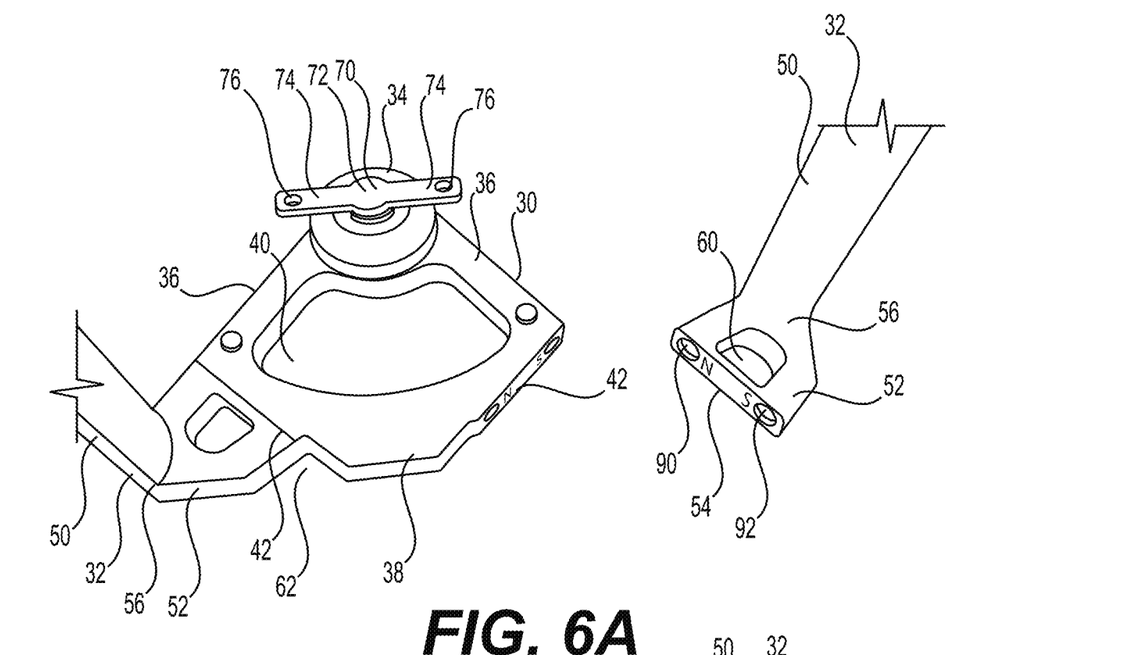
FIGS. 6A-6B show break-away magnetically-attracted deflector legs according to one embodiment.
Figure 6B:
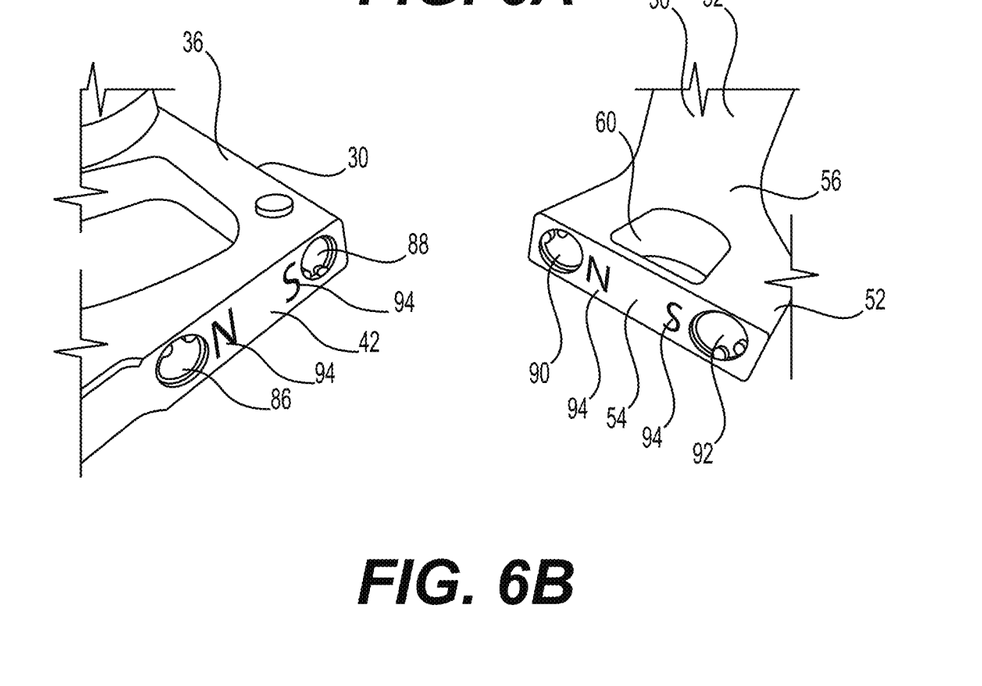

With emphasis on FIGS. 6A-6B, the deflector legs 32 couple to the frame 30 at connection portions 42, 54. Each connection portion 42, 54 may include magnetic attachment points with one or more magnets 86, 88, 90, 92. On the connection portion 42 of the frame 30 for attaching each deflector leg 32, the frame 30 may include a north magnet 86 and a south magnet 88. Similarly, on the connection portion 54 for each deflector leg 32, the shoulder 52 may include a north magnet 90 and a south magnet 92. The magnets 86, 88, 90, 92 may include polar magnets, such as cylinder magnets, disc magnets, bar magnets, rings magnets, etc. It will be appreciated that the locations of north and south magnets may be reversed, the number of magnets may be changed, and the positions of the magnets may be otherwise configured to magnetically attach the deflector legs 32 to the frame 30.

When aligned properly and placed near one another, the north pole of one magnet 86, 90 is attracted to the south pole of the opposite magnet 88, 92. The connection portions 42, 54 may include one or more indictors 94 to identify the polarity of the magnets 86, 88, 90, 92 and/or the proper positioning of the deflector legs 32 relative to the frame 30. In other words, the north and south magnetic attachment points may be arranged and marked in such a way that correct positioning of the left and right deflector legs 32 occur by attracting when correct and repelling when incorrect.

Figure 7:
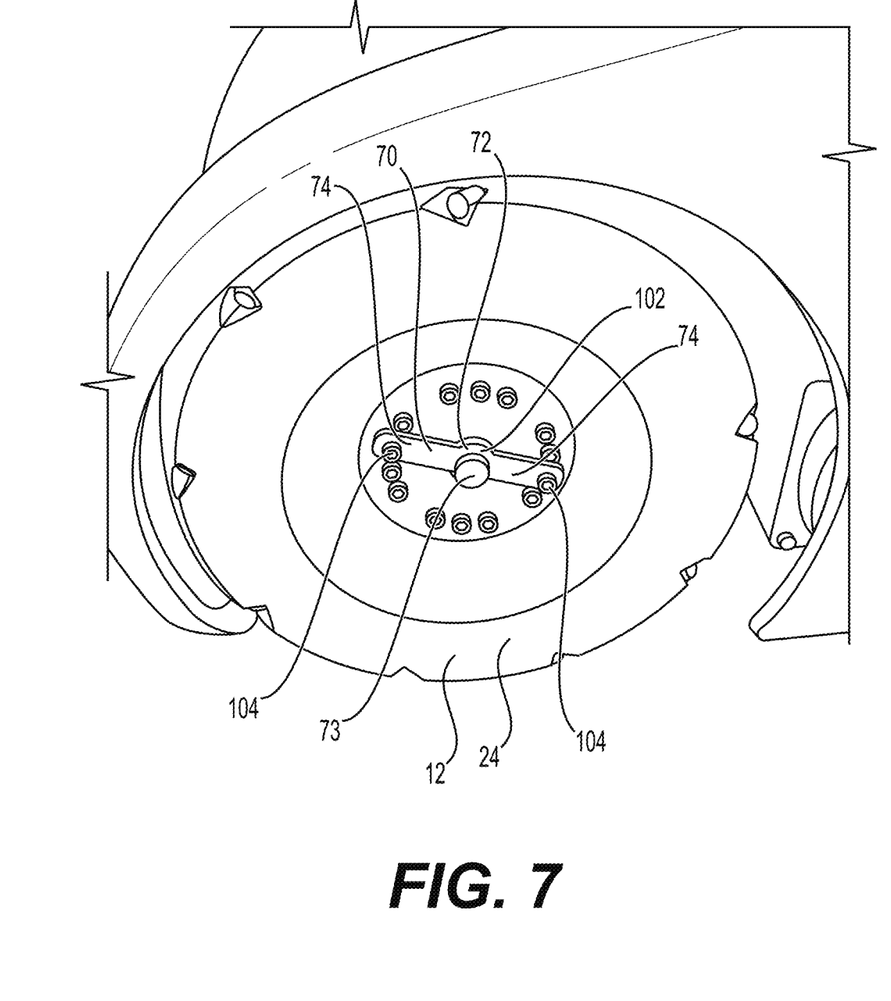
FIG. 7 shows the target mount of the cable protector mounted to the front of the omni-wheel according to one embodiment.
Figure 8:
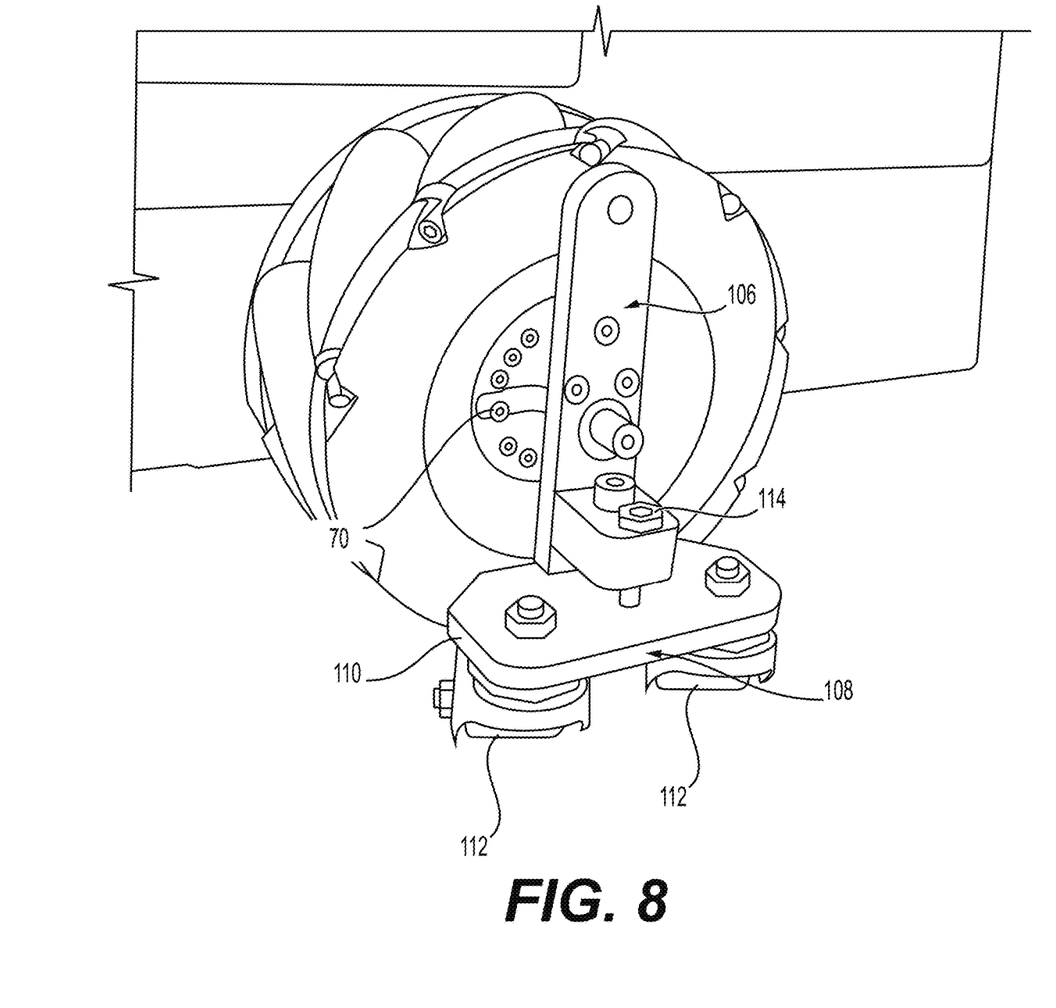
FIG. 8 shows a jack mount screwed onto the target mount for supporting a dolly system according to one embodiment.
Figure 9:
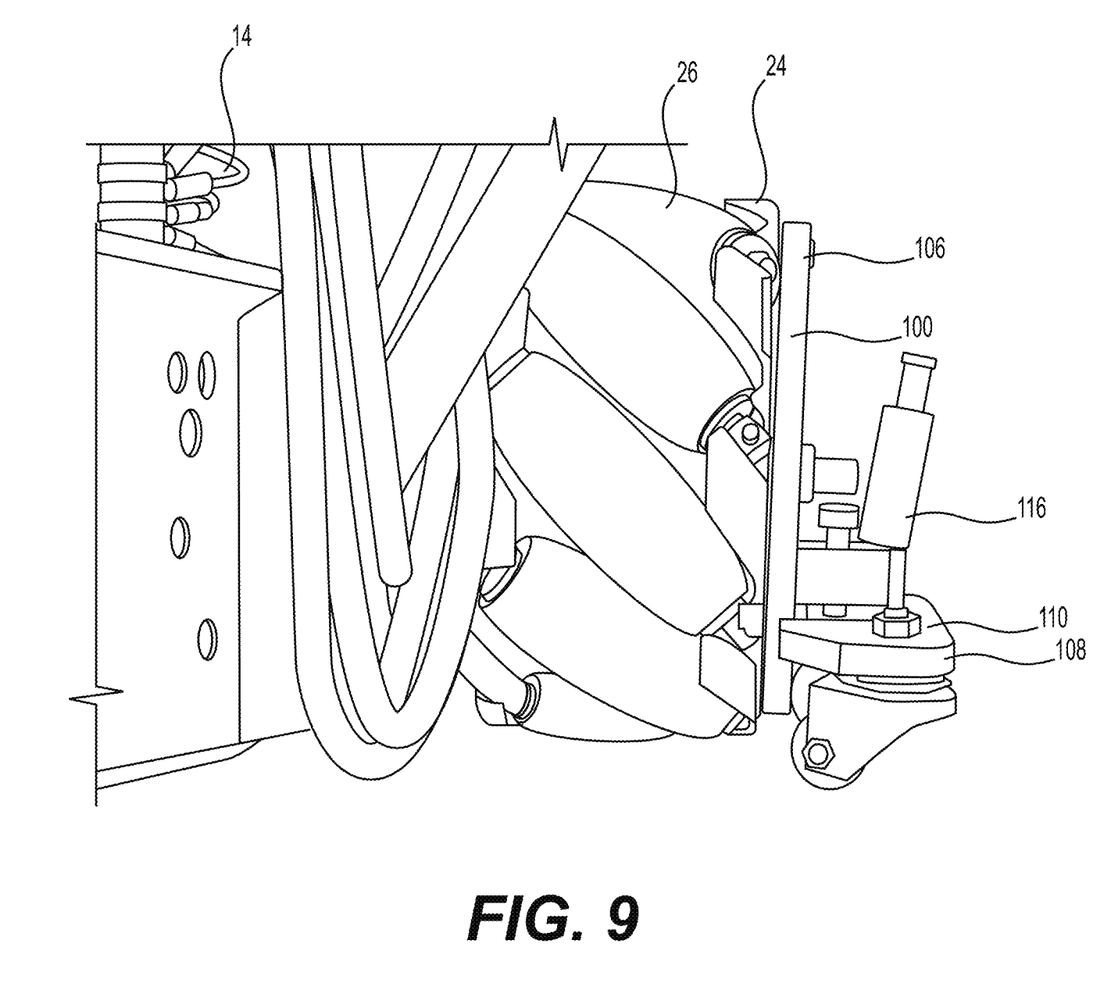
FIG. 9 shows the omni-wheel lifted off the floor via the dolly system according to one embodiment.

Referring now to FIGS. 7-9, the cable pusher target mount 70 allows for attachment of a lifting jack 100 in addition to the cable pushers 10. The target mount 70 that supports the cable pusher assembly 10 magnetically via its front face may also include a threaded interface 102 that can support additional attachments, such as lifting jack 100. As best seen in FIG. 7, the projection 73 on the target mount 70 may include a threaded section 102 with one or more threads around a periphery of the projection 73 configured to mate with corresponding threads on the jack 100. The mount 70 is attached to the wheel hub 24 with nuts 104 secured through openings 76 in the blades 74 of the mount 70.

With further emphasis on FIG. 8, the lifting jack 100 may be secured to the target mount 70 via the threaded interface. The lifting jack 100 may include a jack mount 106, which is shown screwed onto the target mount 70, and a dolly 108. The dolly 108 may include a plate 110 with a plurality of wheels 112 bolted to the plate 110. The dolly wheels 112 may include a pair of caster wheels, for example. The lifting jack 100 may utilize a jacking bolt 114 to raise and lower the wheel 12. As shown in FIG. 9, an instrument 116, such as a socket wrench, may be used to turn the jacking bolt 114, thereby raising wheel 112. As shown in FIG. 9, the omni-wheel 12 is lifted off the floor, thereby allowing for movement of the equipment 14 using the dolly 108. This may be especially helpful in the event of power loss of the moveable system 14. Due to its large mass and the type of omni-wheels 12, the system 14 may be difficult to move manually. By jacking up the two rear wheels 12, for example, via the lifting jack 100 and wheel dolly 108 system, the movable system 14 is more easily maneuvered manually upon power loss. The lifting jack 100 and wheel dolly 108 may assist in the manual movement of the moveable system 14.

The cable protection assembly is configured to protect cables lying on or near the floor from damage by wheels of a moveable system, such as an imaging system. The cable protectors may be especially suitable for use with omni-type wheels that provide for multiple-axis movement of the moveable system. The cable protectors eliminate the need to reach under the wheel to assemble the assembly. Therefore, these cable protectors are less dangerous than snap-together sliding floor ring type protectors used for standard swivel casters. The cable protectors greatly reduce opportunities for breakage of the protectors even upon sudden contact due to the break-away magnetic deflector legs. Minimal sliding contact on the wheels and floor greatly reduce wear and noise since the assemblies hang a slight distance from the floor. Due to the magnetic interface, no tools are required for mounting the cable protectors to the wheels or reassembling after a collision. The cable pusher mount also provides an additional interface for other attachments, such as a wheel jacks.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A cable protection system comprising:
 a moveable system with a plurality of wheels for moving the moveable system across a floor; and
 a cable pusher attached to each of the plurality of wheels, each cable pusher comprising a frame with a pair of deflector legs configured to be positioned in front of and behind each wheel in close proximity to the floor, wherein the cable pusher is magnetically secured to the wheel, and the deflector legs magnetically connect to the frame, and wherein as the wheels spin or rotate, the frame and deflector legs remain stationary, thereby pushing obstacles out of the way.

2. The system of claim 1, wherein each deflector leg includes an elongate leg and a shoulder configured to mate with the frame.

3. The system of claim 2, wherein the shoulder transitions to the leg with a bent portion that positions the leg transverse to the shoulder and the frame when connected thereto.

4. The system of claim 2, wherein the shoulder is bifurcated into two branches by a window, and magnets are positioned in the two branches of the shoulder.

5. The system of claim 1, wherein the pair of deflector legs are aligned in parallel to one another.

6. The system of claim 1, wherein the frame includes an upper hub configured to engage with a wheel hub of the wheel, a pair of angled arms extending distally, and a base connecting the angled arms.

7. The system of claim 6, wherein the upper hub of the frame houses a spinning magnet constrained inside a magnet retainer, wherein the spinning magnet attracts to a magnet on the wheel.

8. The system of claim 1, wherein the cable pusher is attached to the wheel with a mount including a revolving central shaft and a pair of blades positioned on opposite sides of the central shaft.

9. The system of claim 1, wherein the wheels are omni-directional wheels.

10. The system of claim 1, wherein the moveable system is a medical imaging system.

11. A cable pusher assembly comprising:
- a frame including an upper hub, a pair of angled arms, and a base connecting the angled arms, the base including first and second connection areas each including north and south magnets;
- first and second deflector legs each including north and south magnets are configured to magnetically attract to the opposite north and south magnets of the first and second connection areas, respectively, thereby securing the first and second deflector legs to the first and second connection areas of the frame; and
- a target mount including a revolving central shaft and a pair of blades positioned on opposite sides of the central shaft, wherein the upper hub of the frame houses a spinning magnet constrained inside a magnet retainer.

12. The cable pusher assembly of claim 11, wherein the central shaft includes an outward projection on a front face of the mount, and the projection is received in a seat defining a cavity for the projection.

13. The cable pusher assembly of claim 12, wherein the target mount including the central shaft, the seat, the spinning magnet, and the magnet retainer are coaxially aligned along a central axis.

14. The cable pusher assembly of claim 11, wherein the base and the deflector legs include indicators identifying the north and south magnets such that when the deflector legs are correctly positioned against the frame the magnets attract.

15. The cable pusher assembly of claim 11, wherein the magnets are disc magnets.

16. A cable protection system comprising:
- a moveable system with a plurality of wheels for moving the moveable system across a floor;
- a cable pusher attachable to one or more of the plurality of wheels, the cable pusher comprising a frame with a pair of deflector legs and a mount including a revolving central shaft and a pair of blades positioned on opposite sides of the central shaft; and
- a lifting jack attachable to one or more of the plurality of wheels, the lifting jack including a jack mount and a dolly, wherein the lifting jack is configured to lift the wheel off the floor and allow for movement of the moveable system using the dolly.

17. The system of claim 16, wherein the central shaft of the mount includes an outward projection defining a threaded portion configured to theadedly interface with the jack mount.

18. The system of claim 16, wherein the mount is securable to the wheel with nuts positioned through openings in the blades of the mount.

19. The system of claim 16, wherein the lifting jack includes a jacking bolt to raise and lower the wheel.

20. The system of claim 16, wherein the dolly includes a plate with a plurality of caster wheels.

* * * * *